United States Patent [19]

Patard et al.

[11] Patent Number: 5,512,444
[45] Date of Patent: Apr. 30, 1996

[54] METHOD FOR DETERMINING BLADDER TUMORS BY ASSAYING FOR MAGE-1,2,3 OR 4

[75] Inventors: Jean-Jacques Patard; Francis Brasseur; Thierry Boon-Falleur, all of Brussels, Belgium

[73] Assignee: Ludwig Institute For Cancer Research, New York, N.Y.

[21] Appl. No.: 346,774

[22] Filed: Nov. 30, 1994

Related U.S. Application Data

[63] Continuation-in-part of Ser. No. 204,727, Mar. 1, 1994.
[51] Int. Cl.⁶ .............................. C12Q 1/68; C12P 19/34; C07H 21/04; G01N 33/53
[52] U.S. Cl. .................. 435/6; 435/7.1; 435/7.9; 435/91.2; 536/23.1; 536/24.3
[58] Field of Search .................. 435/6, 91.2, 7.1–7.9; 536/23.1, 24.3–24.33

[56] References Cited

FOREIGN PATENT DOCUMENTS

WO9220356 11/1992 WIPO .

OTHER PUBLICATIONS

Van der Bruggen et al., "A Gene Encoding An Antigen Recognized By Cytolytic T Lymphocytes On A Human Melanoma", Science 254: 1643–1647 (Dec. 13, 1991).

Brasseur, et al., "Human gene MAGE-1, which codes for a tumor rejection antigen, is expressed by some breast tumors", Int. J. Cancer 52: 839–841 (1992).

Gaugler et al., "Human Gene MAGE-3 Codes for an Antigen Recognized on a Melanoma by Autologous Cytolytic T Lymphocytes", J. Exp. Med. 179: 921–930 (1994).

*Primary Examiner*—W. Gary Jones
*Assistant Examiner*—Dianne Rees
*Attorney, Agent, or Firm*—Felfe & Lynch

[57] ABSTRACT

A method for screening for bladder cancer by identifying expression of one or more of MAGE-1, MAGE-2, MAGE-3 and MAGE-4 is the disclosed invention. Expression can be determined by a number of methods, including nucleotide amplification assays.

7 Claims, 2 Drawing Sheets

SEQUENCE LISTING ( 1 ) GENERAL INFORMATION:

( i i i ) NUMBER OF SEQUENCES: 10

( 2 ) INFORMATION FOR SEQ ID NO: 1:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1:

```
TGGAGGACCA GAGGCCCCC                                   19
```

( 2 ) INFORMATION FOR SEQ ID NO: 2:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2:

```
GGACGATTAT CAGGAGGCCT GC                               22
```

( 2 ) INFORMATION FOR SEQ ID NO: 3:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 3:

```
CGGCCGAAGG AACCTGACCC AG                               22
```

( 2 ) INFORMATION FOR SEQ ID NO: 4:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 4:

```
GCTGGAACCC TCACTGGGTT GCC                              23
```

( 2 ) INFORMATION FOR SEQ ID NO: 5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 5:

```
AAGTAGGACC CGAGGCACTG                                  20
```

( 2 ) INFORMATION FOR SEQ ID NO: 6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 6:
GAAGAGGAAG AAGCGGTCTG                    20

( 2 ) INFORMATION FOR SEQ ID NO: 7:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 7:
GAGCAGACAG GCCAACCG                      18

( 2 ) INFORMATION FOR SEQ ID NO: 8:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 8:
AAGGACTCTG CGTCAGGC                      18

( 2 ) INFORMATION FOR SEQ ID NO: 9:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 9:
GGGACCAGGA GACACGGAAT A                  21

( 2 ) INFORMATION FOR SEQ ID NO: 10:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 10:
AGCCCGTCCA CGCACCG                       17

METHOD FOR DETERMINING BLADDER TUMORS BY ASSAYING FOR MAGE-1,2,3 OR 4

RELATED APPLICATION

This application is a continuation-in-part of copending application Ser. No. 08/204,727 filed Mar. 1, 1994, incorporated by reference.

FIELD OF THE INVENTION

This invention relates to cancer diagnosis. More particularly, it relates to the "tumor rejection antigen precursors" referred to as MAGE-1, MAGE-2, MAGE-3 and MAGE-4, which have been identified as "markers" for bladder cancers.

BACKGROUND AND PRIOR ART

The study of the recognition or lack of recognition of cancer cells by a host organism has proceeded in many different directions. Understanding of the field presumes some understanding of both basic immunology and oncology.

Early research on mouse tumors revealed that these displayed molecules which led to rejection of tumor cells when transplanted into syngeneic animals. These molecules are "recognized" by T-cells in the recipient animal, and provoke a cytolytic T-cell response with lysis of the transplanted cells. This evidence was first obtained with tumors induced in vitro by chemical carcinogens, such as methylcholanthrene. The antigens expressed by the tumors and which elicited the T-cell response were found to be different for each tumor. See Prehn, et al., J. Natl. Canc. Inst. 18: 769–778 (1957); Klein et al., Cancer Res. 20: 1561–1572 (1960); Gross, Cancer Res. 3: 326–333 (1943), Basombrio, Cancer Res. 30: 2458–2462 (1970) for general teachings on inducing tumors with chemical carcinogens and differences in cell surface antigens. This class of antigens has come to be known as "tumor specific transplantation antigens" or "TSTAs". Following the observation of the presentation of such antigens when induced by chemical carcinogens, similar results were obtained when tumors were induced in vitro via ultraviolet radiation. See Kripke, J. Natl. Canc. Inst. 53: 333–1336 (1974).

While T-cell mediated immune responses were observed for the types of tumor described supra, spontaneous tumors were thought to be generally non-immunogenic. These were therefore believed not to present antigens which provoked a response to the tumor in the tumor carrying subject. See Hewitt, et al., Brit. J. Cancer 33: 241–259 (1976).

The family of tum⁻ antigen presenting cell lines are immunogenic variants obtained by mutagenesis of mouse tumor cells or cell lines, as described by Boon et al., J. Exp. Med. 152: 1184–1193 (1980), the disclosure of which is incorporated by reference. To elaborate, tum⁻ antigens are obtained by mutating tumor cells which do not generate an immune response in syngeneic mice and will form tumors (i.e., "tum⁺" cells). When these tum⁺ cells are mutagenized, they are rejected by syngeneic mice, and fail to form tumors (thus "tum⁻"). See Boon et al., Proc. Natl. Acad. Sci. USA 74: 272 (1977), the disclosure of which is incorporated by reference. Many tumor types have been shown to exhibit this phenomenon. See, e.g., Frost et al., Cancer Res. 43: 125 (1983).

It appears that tum⁻ variants fail to form progressive tumors because they initiate an immune rejection process. The evidence in favor of this hypothesis includes the ability of "tum⁻" variants of tumors, i.e., those which do not normally form tumors, to do so in mice with immune systems suppressed by sublethal irradiation, Van Pel et al., Proc. Natl. Acad. Sci. USA 76: 5282–5285 (1979); and the observation that intraperitoneally injected tum⁻ cells of mastocytoma P815 multiply exponentially for 12–15 days, and then are eliminated in only a few days in the midst of an influx of lymphocytes and macrophages (Uyttenhove et al., J. Exp. Med. 152: 1175–1183 (1980)). Further evidence includes the observation that mice acquire an immune memory which permits them to resist subsequent challenge to the same tum⁻ variant, even when immunosuppressive amounts of radiation are administered with the following challenge of cells (Boon et al., Proco Natl, Acad. Sci. USA 74: 272–275 (1977); Van Pel et al., supra; Uyttenhove et al., supra).

Later research found that when spontaneous tumors were subjected to mutagenesis, immunogenic variants were produced which did generate a response. Indeed, these variants were able to elicit an immune protective response against the original tumor. See Van Pel et al., J. Exp. Med. 157: 1992–2001 (1983). Thus, it has been shown that it is possible to elicit presentation of a so-called "tumor rejection antigen" in a tumor which is a target for a syngeneic rejection response. Similar results have been obtained when foreign genes have been transfected into spontaneous tumors. See Fearon et al., Cancer Res. 48: 2975–1980 (1988) in this regard.

A class of antigens has been recognized which are presented on the surface of tumor cells and are recognized by cytolytic T cells, leading to lysis. This class of antigens will be referred to as "tumor rejection antigens" or "TRAs" hereafter. TRAs may or may not elicit antibody responses. The extent to which these antigens have been studied, has been via cytolytic T cell characterization studies, in vitro i.e., the study of the identification of the antigen by a particular cytolytic T cell ("CTL" hereafter) subset. The subset proliferates upon recognition of the presented tumor rejection antigen, and the cells presenting the antigen are lysed. Characterization studies have identified CTL clones which specifically lyse cells expressing the antigens. Examples of this work may be found in Levy et al., Adv. Cancer Res. 24: 1–59 (1977); Boon et al., J. Exp. Med. 152: 1184–1193 (1980); Brunner et al., J. Immunol. 124: 1627–1634 (1980); Maryanski et al., Eur. J. Immunol. 124: 1627–1634 (1980); Maryanski et al., Eur. J. Immunol. 12: 406–412 (1982); Palladino et al., Canc. Res. 47: 5074–5079 (1987). This type of analysis is required for other types of antigens recognized by CTLs, including minor histocompatibility antigens, the male specific H-Y antigens, and the class of antigens referred to as "tum⁻" antigens, and discussed herein.

A tumor exemplary of the subject matter described supra is known as P815. See DePlaen et al., Proc. Natl. Acad. Sci. USA 85: 2274–2278 (1988); Szikora et al., EMBO J 9: 1041–1050 (1990), and Sibille et al., J. Exp. Med. 172: 35–45 (1990), the disclosures of which are incorporated by reference. The P815 tumor is a mastocytoma, induced in a DBA/2 mouse with methylcholanthrene and cultured as both an in vitro tumor and a cell line. The P815 line has generated many tum⁻ variants following mutagenesis, including variants referred to as P91A (DePlaen, supra), 35B (Szikora, supra), and P198 (Sibille, supra). In contrast to tumor rejection antigens—and this is a key distinction—the tum⁻ antigens are only present after the tumor cells are mutagenized. Tumor rejection antigens are present on cells of a given tumor without mutagenesis. Hence, with reference to the literature, a cell line can be tum+, such as the line referred to as "P1", and can be provoked to produce tum– variants. Since the tum– phenotype differs from that of the parent cell line, one expects a difference in the DNA of tum– cell lines as compared to their tum+ parental lines, and this difference can be exploited to locate the gene of interest in tum– cells. As a result, it was found that genes of tum– variants such as P91A, 35B and P198 differ from their normal alleles by point mutations in the coding regions of the gene. See Szikora and Sibille, supra, and Lurquin et al., Cell 58: 293–303 (1989). This has proved not to be the case with the TRAs of this invention. These papers also demonstrated that peptides derived from the tum– antigen are presented by the $L^d$ molecule for recognition by CTLs. P91A is presented by $L^d$, P35 by $D^d$ and P198 by $K^d$.

PCT application U.S. Pat. No. 92/04354, filed on May 22, 1992 assigned to the same assignee as the subject application, teaches a family of human tumor rejection antigen precursor coding genes, referred to as the MAGE family. Several of these genes are also discussed in van der Bruggen et al., Science 254: 1643 (1991). It is now clear that the various genes of the MAGE family are expressed in tumor cells, and can serve as markers for the diagnosis of such tumors, as well as for other purposes discussed therein. A U.S. application corresponding in part to this PCT application has issued as U.S. Pat. No. 5,342,774, and is incorporated by reference herein. See also Traversari et al., Immunogenetics 35: 145 (1992); van der Bruggen et al., Science 254: 1643 (1991). The mechanism by which a protein is processed and presented on a cell surface has now been fairly well documented. A cursory review of the development of the field may be found in Barinaga, "Getting Some 'Backbone': How MHC Binds Peptides", Science 257: 880 (1992); also, see Fremont et al., Science 257: 919 (1992); Matsumura et al., Science 257: 927 (1992); Latron et al., Science 257: 964 (1992). These papers generally point to a requirement that the peptide which binds to an MHC/HLA molecule be nine amino acids long (a "nonapeptide"), and to the importance of the first and ninth residues of the nonapeptide.

Studies on the MAGE family of genes have now revealed that, in some cases a nonapeptide is presented on the surface of tumor cells, and that the presentation of the nonapeptide requires that the presenting molecule be HLA-A1. Complexes of the MAGE-1 tumor rejection antigen (the "TRA" or nonapeptide") lead to lysis of the cell presenting them by cytolytic T cells ("CTLs"). Additional research has correlated other nonapeptides derived from MAGE and genes to HLA-A1 and other MHC class I molecules.

Research presented in, e.g., U.S. patent application Ser. No. 07/938,334 filed Aug. 31, 1992, showed that, when comparing homologous regions of various MAGE genes to the region of the MAGE-1 gene coding for the relevant nonapeptide, there is a great deal of homology.

The nucleic acid sequences which code for the nonapeptides were also described therein. These nucleic acid sequences were described as also being useful as diagnostic probes for tumor presence.

The application also showed how it had been found that a cellular model could be used, wherein a non-human cell can be transfected with a nucleic acid sequence coding for a human HLA molecule. The resulting transfectant could then be used to test for nonapeptide specificity of the particular HLA molecule, or as the object of a second transfection with a MAGE gene. The co-transfectant could be used to determine whether the particular MAGE based TRA is presented by the particular HLA molecule.

Many of the references referred to supra present data on the expression pattern of various MAGE genes in different types of cell lines and tumor tissues. What is evident from these data is that there is no "unifying principle" which allows one to predict which MAGE gene will be expressed by a particular tumor type. Thus, while on one level one can say that MAGE genes are "markers" for tumors, on the level of specific tumor types, the correlation of marker and tumor type is not predictable, and must be determined empirically.

This invention relates to the identification of expression of the MAGE-1, 2, 3, and 4 in bladder cancer. Methods for determining presence of these conditions, and reagents useful in the assays, are the subject matter of the invention.

DETAILED DESCRIPTION OF PREFERRED EMBODIMENTS

EXAMPLE 1

Figure 1:
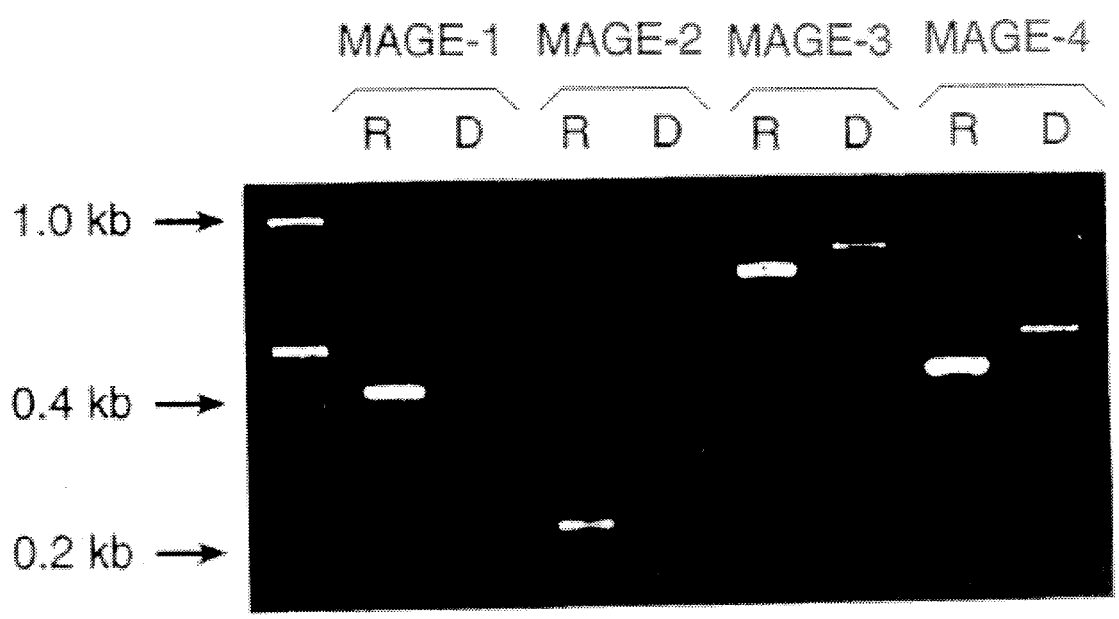
FIG. 1 shows reverse transcription/PCR amplification production of mRNA extracted from the bladder tumor of a patient referred to as "HM15". This is shown in all lanes marked "R". In lanes marked D, amplification products of the genomic DNA from the patient are shown.

The expression of the MAGE-3 gene in various tumors and normal tissues was evaluated, using both reverse transcription and polymerase chain reaction ("PCR") amplification. To perform these assays, the total RNA of the cells of interest was extracted via the well known guanidine-isothiocyanate procedure of Davis et al., Basic Methods in Molecular Biology, 1986 (New York, Elsevier, pp. 130), which is incorporated by reference in its entirety. cDNA was then synthesized, by taking 2 ug of the RNA, diluting it with water, and then adding the following materials: 4 ul of 5× reverse transcriptase buffer, 1 ul each of each dNTP (10 mM), 2 ul of a 20 µM solution of oligo dT, 20 units of RNAsin, 2 ul of 0.1M dithiothreitol, and 200 units of MoMLV reverse transcriptase. All materials were mixed in a 20 ul reaction volume, and incubated at 42° C. for 60 minutes. For the amplification reaction, 1/20 of the cDNA reaction product was supplemented with 5 ul of PCR buffer, 0.5 ul of each of the dNTPs (10 mM), 1 ul each of 20 µM solutions of primer (see infra), and 1.25 units of Taq polymerase. Water was added to a final volume of 50 uls. The primers used for MAGE-3 were:

5'-TGGAGGACCAGAGGCCCCC-3'
(SEQ ID NO: 1)
5'-GGACGATTATCAGGAGGCCTGC-3'
(SEQ ID NO: 2)

These correspond to a sense sequence in exon 2 of the gene (SEQ ID NO: 1), and an antisense sequence in exon 3 (SEQ ID NO: 2).

PCR was performed for 30 cycles (one minute at 94° C., four minutes at 72° C). PCR products were size fractionated on a 1% agarose gel, and then analyzed. The results are presented in the table which follows. These data confirm some results obtained previously, but also show the expression of MAGE-3 in head and neck squamous cell carcinomas, a result not suggested by previous work.

TABLE 1

Expression of gene MAGE-3 by tumoral, normal and fetal tissues.

| TUMORS HISTOLOGICAL TYPE: | Number of MAGE-3 positive tumors* cell lines | tumors samples | NORMAL TISSUES HISTOLOGICAL TYPE | MAGE-3 expression* |
|---|---|---|---|---|
| Melanomas | 50/62 (81%) | 72/105 (69%) | ADULT TISSUES | |
| Head and neck squamous cell carcinomas | — | 20/36 (56%) | Brain | − |
| NSCLC | 1/2 | 14/46 (30%) | Colon | − |
| SCLC | 18/22 (82%) | 2/3 | Stomach | − |
| Colorectal carcinomas | 5/16 | 5/31 (16%) | Liver | − |
| Manmary carcinomas | 2/6 | 16/132 (12%) | Skin | − |
| Bladder tumors | — | 2/6 | Lung | − |
| Sarcomas | 1/4 | 3/10 | Kidney | − |
| Prostatic carcinomas | — | 3/20 | Breast | − |
| Renal carcinomas | 0/5 | 0/38 | Testis | ++ |
| Leukemias | 2/6 | 0/20 | FETAL TISSUES | |
| Lymphomas | 0/6 | 0/5 | Brain | − |
| | | | Liver | − |
| | | | Spleen | − |

*Expression of gene MAGE-3 was tested by RT-PCR amplification on total RNA, with the primers described in methods. These primers distinguish MAGE-3 from the 11 other MAGE genes that have been identified.
‡NSCLC are non-small cell lung carcinomas, SCLC are small cell lung carcinomas.

EXAMPLE 2

Bladder tumor specimens were collected at surgery. They were divided into two portions, one of which was used for routine histopathological evaluation. The other portion was frozen in liquid nitrogen immediately after transurethral resection, or radical cystectomy. These frozen samples were stored at −80° C. until used for RNA extraction. Normal bladder tissue was obtained by biopsies of cadavers from donors in an organ transplant program.

Total RNA was extracted from the samples by the classic guanidine-isothiocyanate/cesium chloride method of Davis et al, *Basic Methods in Molecular Biology*, pp. 130–135, Elsevier, N.Y. (1986). Synthesis of cDNA was then carried out by extension with oligo(dT) using 2 ug of RNA in a 20 ul reaction volume following DeSmet et al., Immunogenetics 39: 121–129 (1994), incorporated by reference herein. Following incubation at 42° C. for one hour, the cDNA reaction mixture was diluted to 100 ul with water. Separate polymerase chain reaction amplification were then carried out to determine whether any of MAGE-1, 2, 3 or 4 cDNA were present. The amplifications were carried out using oligonucleotide primers located in different exons of the MAGE genes. PCR amplification was also carried out using primers for HLA-A1.

The primers used were the following:

5'-TGGAGGACCAGAGGCCCCC-3 (sense, exon 2) (SEQ ID NO: 1) and
5'-GGACGATTATCAGGAGGCCTGC-3' (antisense, exon 3) (SEQ ID NO: 2) for MAGE-3
5'-CGGCCGAAGGAACCTGACCCAG-3' (sense, exon 1) (SEQ ID NO: 3) and
5'GCTGGAACCCTCACTGGGTTGCC-3' (anti-sense, exon 3) (SEQ ID NO: 4) for MAGE-1
5'-AAGTAGGACCCGAGGCACTG-3' (sense, exon 2) (SEQ ID NO: 5) and
5'-GAAGAGGAAGAAGCGGTCTG-3' (anti-sense, exon 3) (SEQ ID NO: 6) for MAGE-2
5'-GAGCAGACAGGCCAACCG-3' (sense, exon 2) (SEQ ID NO: 7) and
5'-AAGGACTCTGCGTCAGGC-3' (anti-sense, exon 3) (SEQ ID NO: 8) for MAGE-4
5'-GGGACCAGGAGACACGGAATA-3' (sense, exon 2) (SEQ ID NO: 9) and
5'-AGCCCGTCCACGCACCG-3' (anti-sense, exon 3) (SEQ ID NO: 10) for HLA-A1

SEQ ID NOS: 1 and 2 are described by Weynants et al., Int. J. Cancer 56: 826–829 (1994). SEQ ID NOS: 3 and 4 are described in Brasseur et al., Int. J. Cancer 52: 839–841 (1992). SEQ ID NOS: 5 and 6 are disclosed in DeSmet et al., Immunogenetics 39: 121–129 (1994). SEQ ID NOS: 7 and 8 are disclosed in copending application Ser. No. 08/299,849 filed Sep. 1, 1994 to DePlaen et al., and incorporated by reference. SEQ ID NOS: 9 and 10 are found in Gaugler et al., J. Exp. Med. 179: 921–930 (1994), as well as the above-identified parent application. All of these references are incorporated by reference.

The amplification protocol was as follows. Each PCR reaction used 5 ul of cDNA, supplemented with 5 ul of 10x PCR buffer, 1 ul each of 10 mMdNTP, 0.5 ul each of 80 uM solutions of primers, 1.25 units of Taq DNA polymerase, and water to achieve a total volume of 50 ul. The mixtures were heated to 94° C. for 5 minutes, followed by amplification in a thermal cycler, for 30 cycles. For MAGE-1, 1 cycle was one minute at 94° C. followed by three minutes at 72° C. For MAGE-2, one cycle was 94° C. for one minute, followed by two minutes at 67° C. and two minutes at 72° C. For MAGE-3, one cycle was one minute at 94° C., followed by four minutes at 72° C. For MAGE-4, one cycle was one minute at 94° C. two minutes at 68° C. and two minutes at 72° C. The cycle for HLA-A1 was the same as that for MAGE-4. A 10 ul sample of each reaction was run on a 1% agarose gel, and then visualized by ethidium bromide fluorescence. In order to provide a control for RNA integrity, a 20 cycle PCR assay, using primers specific for β actin, was carried out in each case, following Weynants et al., supra.

The protocols described were developed with certain goals in mind. Primers were selected so as to be in different exons, thus preventing false positives due to DNA contamination of the RNA preparations. Under the conditions used, DNA generates either no PCR product, or longer products which are readily distinguishable from amplified cDNA. This is shown by FIG. 1. In FIG. 1, a bladder tumor sample from a patient, referred to as "HM15" is shown in each "R" lane. Lanes marked "D" show products obtained from amplification of the patients' genomic DNA. The PCR products were run on a 2.5% low melting agarose gel, but the assays were identical to the protocol of this example in all other ways. Size markers are on the left hand side. There was no band in the MAGE-1 reaction, because of the large intron between the two primers.

Figure 2:
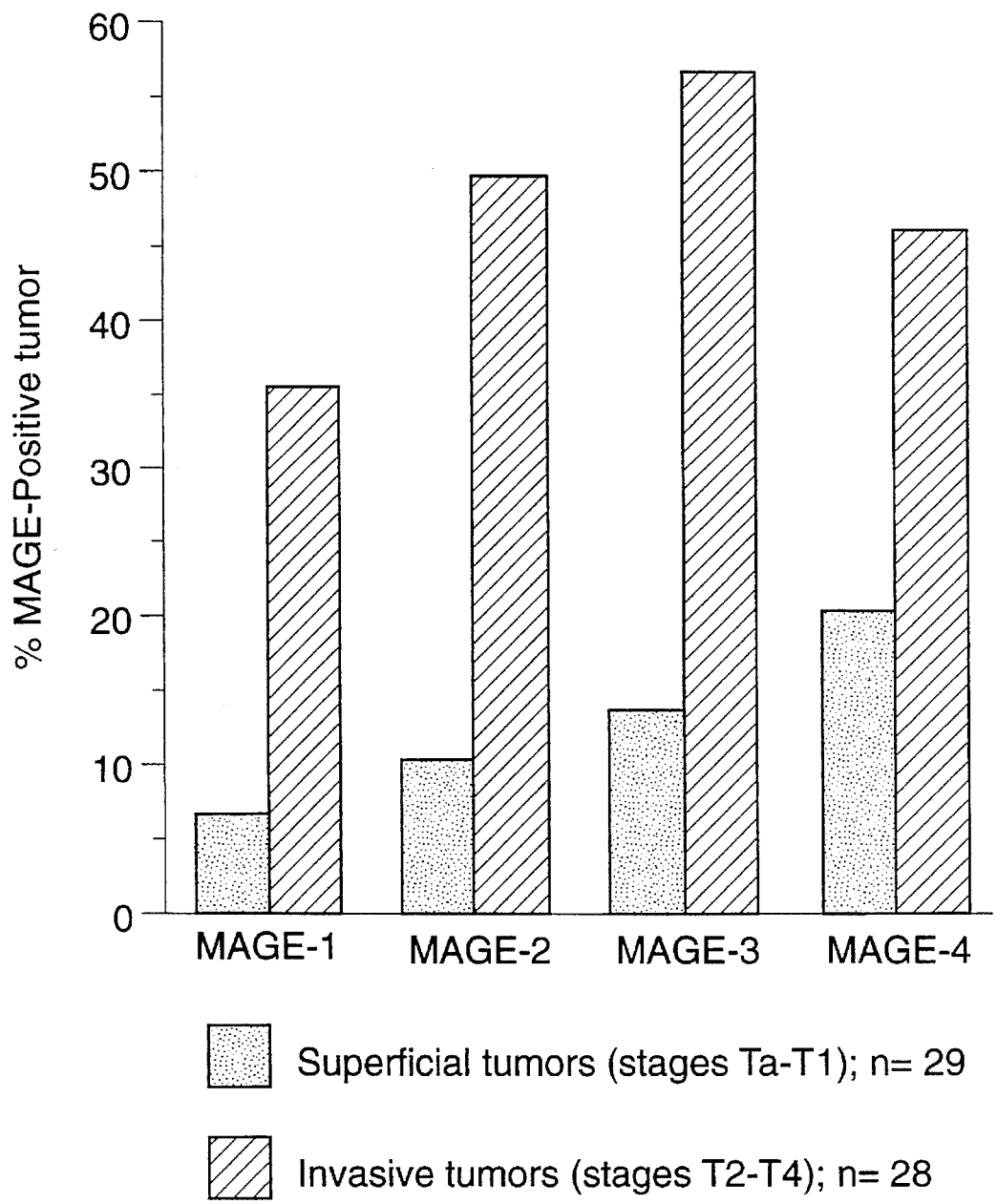
FIG. 2 displays the fractions of tumors expressing genes MAGE-1, 2, 3 and 4 among superficial and invasive transitional cell carcinomas of the bladder.

Table 2, which follows, shows the results obtained for a number of tumors (nomenclature is explained below). Of 57 samples of primary transitional cell carcinoma, 21% expressed MAGE-1, 30% expressed MAGE-2, 35% expressed MAGE-3, and 33% expressed MAGE-4. Ta tumors and low grade T1 tumors expressed none of these, or expressed only a single gene, at low levels. Higher stage tumors, in contrast, frequently expressed high levels of several genes. It was also found that the fraction of invasive tumors which expressed MAGE genes was 2–5 times higher than the fraction observed with superficial tumors, as is depicted in FIG. 2 (this figure is based upon data from Table 2). Tumors expressing at least one of the four MAGE genes accounted for 61% of the 28 invasive tumors studied. Among the 29 superficial tumors, the proportion was only 28%. Results paralleled other results reported previously for melanoma, in that all but one of the tumors expressing MAGE-1 also expressed MAGE-3.

None of the six biopsies of normal bladder examined expressed any of the MAGE genes discussed herein.

In some instances, several tumor samples were obtained from the same patient. The analysis of these patients is set out in Table 3. Patient HM61 had a primary tumor and an invaded lymph node. They displayed a very similar pattern of expression of MAGE-1, 2, and 3, with MAGE-1 predominating. Normal mucosa adjacent to the tumor was completely negative for MAGE-2 and MAGE-3, with a very low level of MAGE-1 expression, which was probably due to the presence of a few tumor cells. In patient "HM25", the initial tumor, and an early recurrence, both expressed MAGE-1, 2, 3 and 4. A recurrence which occurred two years after the first displayed a very different pattern, expressing only MAGE-2 and MAGE-3. A similar discordance between primary tumor and recurrence was observed with patient "HM20". Patients HM30 and LB526 showed differences in the pattern of MAGE-expression in different samples of the same primary tumor.

In the tables which follow, "Ta" stands for a superficial lesion, limited to bladder mucosa (also known as "stage Ta"). "Stage T1", or "T1" is used for superficial lesions limited to subepithelial connective tissue "Stages T2–T4", or "T2–T4" refer to tumors which have invaded bladder muscle. The nomenclature "G1", "G2" and "G3" refers to the degree of differentiation, or histopathological grade. "G1" superficial tumor is well differentiated, while a "G3" tumor is poorly differentiated. See Mostofi et al., "Histological Typing of Urinary Bladder Tumors. WHO International Histological Classification of Tumors" (1973).

TABLE II

EXPRESSION OF GENES MAGE-1, 2, 3 AND 4 IN MULTIPLE SAMPLES FROM BLADDER CARCINOMA PATIENTS

| Patients | Samples | Tumor stage and grade | MAGE-1 | MAGE-2 | MAGE-3 | MAGE-4 |
|---|---|---|---|---|---|---|
| HM 61 | Primary tumor | T2 G3 | ++ | + | + | − |
|  | Metastatic iliac lymph node |  | +++ | + | + | − |
|  | Mucosa adjacent to the tumor |  | + | − | − | − |
| HM 25 | Primary tumor | T2 G2 | + | ++ | + | ++ |
|  | Tumor recurrence after 1 month | T2 G2 | ++ | ++ | ++ | ++ |
|  | Tumor recurrence after 2 years | T1 G2 | − | +++ | +++ | − |
| HM 20 | Primary tumor | T1 G1 | + | − | − | − |
|  | Tumor recurrence after 2 months | T1 G1 | − | − | − | − |
| HM 30 | Primary tumor, 1st sample | T2 G2 | − | − | ++ | − |
|  | Primary tumor, 2nd sample | T2 G2 | − | − | − | − |
| LB 526 | Primary tumor, radical cystectomy | T3 G2 | + | + | ++ | + |
|  | Primary tumor, 9-day pre-operative biopsy | T3 G2 | + | + | + | − |

TABLE 3

EXPRESSION OF GENES MAGE-1, 2, 3 AND 4 IN BLADDER TRANSITIONAL-CELL CARCINOMA SAMPLES

| Tumor Stage and Grade‡ | | Patients | | MAGE-1 | MAGE-2 | MAGE-3 | MAGE-4¶ |
|---|---|---|---|---|---|---|---|
| Superficial tumors (n = 29) | | | | | | | |
| Ta (n = 7) | G1 | HM 7 | | − | − | + | − |
|  |  | HM 32 | (A1)* | − | − | − | − |
|  |  | HM 33 | (A1) | − | − | − | − |
|  |  | HM 49 | | − | − | − | − |
|  | G2 | LB 523 | | − | − | − | − |
|  |  | LB 817 | | − | − | − | − |
|  |  | LB 818 | | − | − | − | − |
| T1 (n = 22) | G1 | HM 2 | | − | − | − | − |
|  |  | HM 6 | (A1) | − | − | − | − |
|  |  | HM 17 | | − | − | − | − |
|  |  | HM 20 | | + | − | − | − |

TABLE 3-continued

EXPRESSION OF GENES MAGE-1, 2, 3 AND 4 IN BLADDER TRANSITIONAL-CELL CARCINOMA SAMPLES

| Tumor Stage and Grade‡ | | Patients | | MAGE-1 | MAGE-2 | MAGE-3 | MAGE-4¶ |
|---|---|---|---|---|---|---|---|
| | | HM 22 | | − | − | − | − |
| | | HM 34 | | − | − | − | − |
| | | HM 35 | | − | − | − | + |
| | G2 | HM 4 | | − | + | + | + |
| | | HM 5 | | − | − | − | − |
| | | HM 9 | | − | − | − | − |
| | | HM 27 | | − | − | − | +++ |
| | | HM 37 | | − | − | − | − |
| | | HM 38 | (A1) | − | − | − | − |
| | | HM 39 | | − | − | − | + |
| | | HM 40 | (A1) | − | − | − | − |
| | | HM 41 | | − | − | − | − |
| | G3 | HM 14 | | ++ | +++ | +++ | ++ |
| | | HM 23 | | − | − | − | − |
| | | HM 26 | | − | +++ | +++ | +++ |
| | | HM 42 | (A1) | − | − | − | − |
| | | HM 53 | | − | − | − | − |
| | | LB 767 | (A1) | − | − | − | − |
| Invasive tumors (n = 28) | | | | | | | |
| T2 (n = 5) | G2 | HM 8 | | − | − | − | − |
| | | HM 13 | (A1) | − | − | − | − |
| | | HM 24 | (A1) | + | +++ | +++ | ++ |
| | | HM 25 | | + | ++ | + | ++ |
| | | HM 30 | | − | − | ++ | − |
| | | LB 796 | | − | − | − | − |
| | G3 | HM 3 | (A1) | − | − | − | − |
| | | HM 10 | | − | + | ++ | ++ |
| | | HM 12 | | − | + | + | − |
| | | HM 15 | | +++ | +++ | +++ | +++ |
| | | HM 61 | (A1) | ++ | + | + | − |
| | | LB 524 | (A1) | − | − | +++ | + |
| | | LB 824 | | − | ++ | +++ | + |
| | | LB 825 | | + | ++ | + | + |
| | | LB 831 | | + | ++ | +++ | ++ |
| T3 (n = 11) | G2 | HM 44 | | − | − | − | − |
| | | HM 45 | | − | +++ | +++ | − |
| | | HM 46 | (A1) | − | − | − | − |
| | | LB 526 | | + | + | ++ | + |
| | G3 | HM 11 | | ++ | + | ++ | + |
| | | HM 18 | | − | − | − | − |
| | | HM 21 | | − | − | − | − |
| | | HM 47 | | +++ | +++ | +++ | +++ |
| | | EM 48 | | − | − | − | − |
| | | HM 50 | | +++ | +++ | +++ | + |
| | | HM 52 | (A1) | − | − | − | − |
| T4 (n = 2) | G3 | HM 1 | | − | − | − | + |
| | | HM 51 | | − | − | − | − |

The foregoing examples demonstrate that by identifying expression of any of MAGE-1, 2, 3 or 4 in a bladder tissue sample, one can diagnose for bladder cancer. None of these genes are expressed in normal bladder tissue, and all have been shown to be expressed in the tumor samples tested, taken directly from patients.

The examples demonstrate amplification methodologies, e.g., PCR, for determination of expression of the genes. This is by no means the only way to carry out the assay. U.S. Pat. No. 5,342,774, incorporated by reference, sets forth the nucleotide sequences for all of these genes. As the current application shows that the genes are expressed in bladder tumors, one can use the known sequences to develop probes useful in any of the standard nucleic acid molecule hybridization assays well known in the art. See, e.g., Keller, *DNA Probes* (1989), incorporated by reference, for a number of these assays using both unlabelled and labelled probes.

Similarly, the sequences of the tumor rejection antigen precursors are provided by the above-identified patent, thus allowing the skilled artisan to develop assays based on protein-binding partner assays, such as immunoassays.

The recognition that normal bladder tissue does not express MAGE genes means that one must assume that these genes are "turned on" in cancer cells at some point in malignant transformation and/or progression. The difference in expression patterns suggests a means for differentiating primary tumors and recurrences, as the latter could originate from different preneoplastic or early neoplastic lesions, such as dysplasia or carcinoma in situ, which acquire different patterns of expression at malignancy. In addition, the data regarding differences in pattern of expression from the same primary tumor suggest that activation can also occur in cells which are already part of a malignant lesion.

Of all samples tested, 37% of bladder transitional-cell carcinomas expressed MAGE-1 or MAGE-3. Thus, it is clear that a diagnostic assay as described supra is set forth by this application, as are assays to determine tumor progression.

Other aspects of the invention will be clear to the skilled artisan and need not be reiterated here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

What is claimed is:

1. Method for screening for bladder cancer in a subject, comprising assaying a bladder tissue sample from a subject to determine expression of mRNA of at least one member of the group of genes encoding MAGE-1, MAGE-2, MAGE-3 and MAGE-4 tumor rejection antigen precursors, wherein expression of said mRNA is an indication of possibility of bladder cancer in said subject.

2. The method of claim 1, comprising determining said mRNA expression via a nucleic acid amplification assay.

3. The method of claim 2, wherein said amplification assay is polymerase chain reaction.

4. The method of claim 3, comprising carrying out polymerase chain reaction with a pair of primers selected from the group consisting of: (i) SEQ ID NO: 1 and SEQ ID NO: 2; (ii) SEQ ID NO: 3 and SEQ ID NO: 4; (iii) SEQ ID NO: 5 and SEQ ID NO: 6; (iv) SEQ ID NO: 7 and SEQ ID NO: 8, and (v) SEQ ID NO: 9 and SEQ ID NO: 10.

5. Method for screening for bladder cancer in a subject, comprising assaying a bladder tissue sample from a subject to determine presence of at least one member of the group of MAGE-1, MAGE-2, MAGE-3 and MAGE-4 tumor rejection antigen precursors in said sample is an indication of possibility of bladder cancer in said subject.

6. The method of claim 5, comprising determining saw at least one of said tumor rejections antigen precursors in an immunoassay.

7. Method for monitoring status of a bladder cancer comprising:

(i) assaying a sample of bladder cancer cells taken from a subject with bladder cancer to determine expression of mRNA for at least one member of the group of genes encoding MAGE-1, MAGE-2 MAGE-3 and MAGE-4 tumor rejections antigen precursors, to determine a value, wherein said value is the level of mRNA expression in said sample and (ii) comparing the value determined in (i) to a value determined previously for the member or members of the group of genes encoding MAGE-1, MAGE-2, MAGE-3 and MAGE-4 tumor rejection antigen precursors obtained the same way the value in (i) was determined, wherein a change in the value obtained in (i) as compared to the value determined previously shows a change in status of said bladder cancer.

* * * * *